United States Patent
Irisawa et al.

(10) Patent No.: US 9,791,417 B2
(45) Date of Patent: Oct. 17, 2017

(54) ACOUSTIC WAVE DETECTION PROBE AND PHOTOACOUSTIC MEASUREMENT APPARATUS PROVIDED WITH THE SAME

(71) Applicant: FUJIFILM Corporation, Minato-ku, Tokyo (JP)

(72) Inventors: Kaku Irisawa, Ashigarakami-gun (JP); Katsuya Yamamoto, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 525 days.

(21) Appl. No.: 14/457,751

(22) Filed: Aug. 12, 2014

(65) Prior Publication Data

US 2014/0345385 A1 Nov. 27, 2014

Related U.S. Application Data

(63) Continuation of application No. PCT/JP2013/000659, filed on Feb. 7, 2013.

(30) Foreign Application Priority Data

Feb. 13, 2012 (JP) .................................. 2012-028372
Feb. 4, 2013 (JP) .................................. 2013-019302

(51) Int. Cl.
*G01N 29/24* (2006.01)
*A61B 8/00* (2006.01)
(Continued)

(52) U.S. Cl.
CPC ............ *G01N 29/22* (2013.01); *A61B 5/0035* (2013.01); *A61B 5/0095* (2013.01);
(Continued)

(58) Field of Classification Search
CPC .... G01N 29/22; G01N 29/043; G01N 29/221; G01N 29/2418; G01N 29/2456;
(Continued)

(56) References Cited

U.S. PATENT DOCUMENTS

| 4,651,850 A | 3/1987 | Matsuo | |
|---|---|---|---|
| 2003/0181802 A1* | 9/2003 | Ogawa | G01H 9/004 600/407 |

(Continued)

FOREIGN PATENT DOCUMENTS

| JP | 58-216294 A | 12/1983 |
|---|---|---|
| JP | 2005-125071 A | 5/2005 |

(Continued)

OTHER PUBLICATIONS

Japanese Office Action for Japanese Application No. 2013-019302, dated May 12, 2015, with a machine translation.

(Continued)

*Primary Examiner* — Laura Martin
*Assistant Examiner* — Rose M Miller
(74) *Attorney, Agent, or Firm* — Birch, Stewart, Kolasch & Birch, LLP

(57) ABSTRACT

An acoustic wave detection probe includes a light projection section that emits measuring light to be projected onto a subject, an acoustic wave transducer disposed adjacent to the light projection section and capable of detecting an acoustic wave, an acoustic lens provided on a detection side of the acoustic wave transducer, and a housing accommodating the light projection section, the acoustic wave transducer, and the acoustic lens, in which the acoustic lens and a surface portion of the housing adjacent to the acoustic lens are formed to have an optical property in which the average diffuse reflection factor is 85% or more and the average absorption factor is 10% or less in a wavelength range of the measuring light.

19 Claims, 6 Drawing Sheets

(51) Int. Cl.
  *G01N 29/22* (2006.01)
  *A61B 5/00* (2006.01)
  *G01N 29/04* (2006.01)
  *B06B 1/06* (2006.01)

(52) U.S. Cl.
  CPC .......... *A61B 8/4416* (2013.01); *B06B 1/0644* (2013.01); *G01N 29/043* (2013.01); *G01N 29/221* (2013.01); *G01N 29/2418* (2013.01); *G01N 29/2437* (2013.01)

(58) Field of Classification Search
  CPC ........... G01N 29/2437; G01N 21/1702; G01N 21/1706; G01N 21/1708; A61B 5/0035; A61B 5/0093; A61B 5/0095
  USPC ........................... 73/609, 642, 643, 644, 617
  See application file for complete search history.

(56) References Cited

U.S. PATENT DOCUMENTS

| | | |
|---|---|---|
| 2005/0070801 A1 | 3/2005 | Yamashita et al. |
| 2009/0005685 A1 | 1/2009 | Nagae et al. |
| 2009/0024038 A1* | 1/2009 | Arnold ................. A61B 5/0095 600/459 |
| 2009/0069486 A1 | 3/2009 | Yamashita et al. |
| 2009/0243436 A1 | 10/2009 | Rubinsztajn et al. |
| 2010/0053618 A1 | 3/2010 | Nakajima et al. |
| 2011/0112406 A1 | 5/2011 | Rubinsztajn et al. |
| 2012/0133941 A1 | 5/2012 | Nakajima et al. |
| 2012/0329904 A1 | 12/2012 | Suita et al. |
| 2013/0109950 A1* | 5/2013 | Herzog ................. A61B 8/0825 600/407 |
| 2013/0289381 A1* | 10/2013 | Oraevsky ............. A61B 5/7425 600/407 |

FOREIGN PATENT DOCUMENTS

| | | |
|---|---|---|
| JP | 2009-31268 A | 2/2009 |
| JP | 2009-240782 A | 10/2009 |
| JP | 2010-75681 A | 4/2010 |
| JP | 2011-209691 A | 10/2011 |
| WO | WO 2013/018313 A1 | 2/2013 |

OTHER PUBLICATIONS

International Search Report, issued in PCT/JP2013/000659, dated Apr. 9, 2013.
Japanese Notification of Reasons for Refusal, dated Aug. 23, 2016, for corresponding Japanese Application No. 2015-248181, along with an English translation.

* cited by examiner

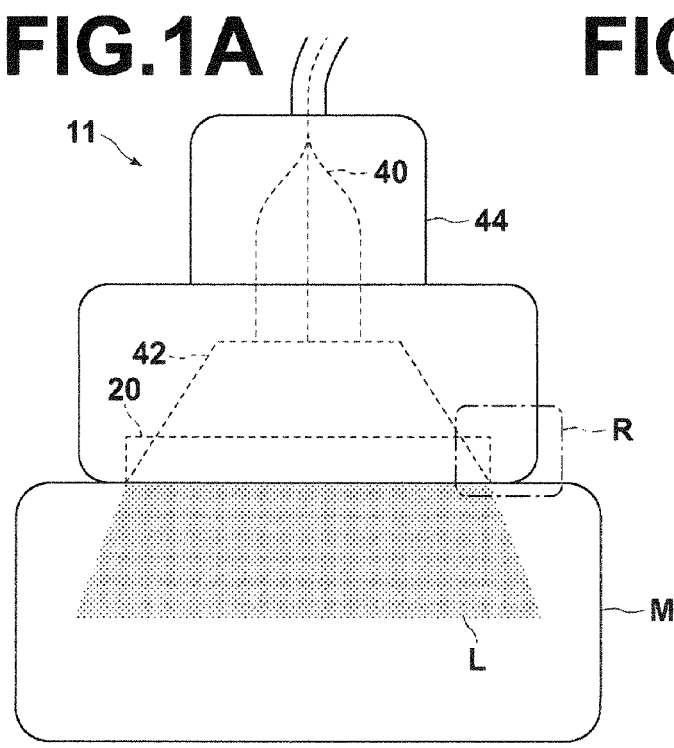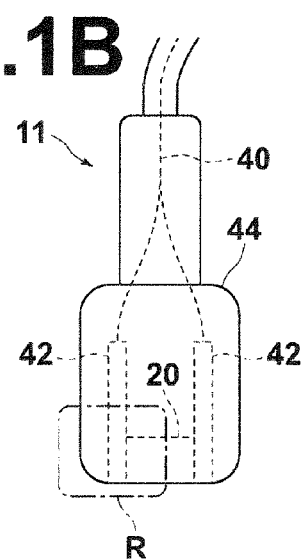

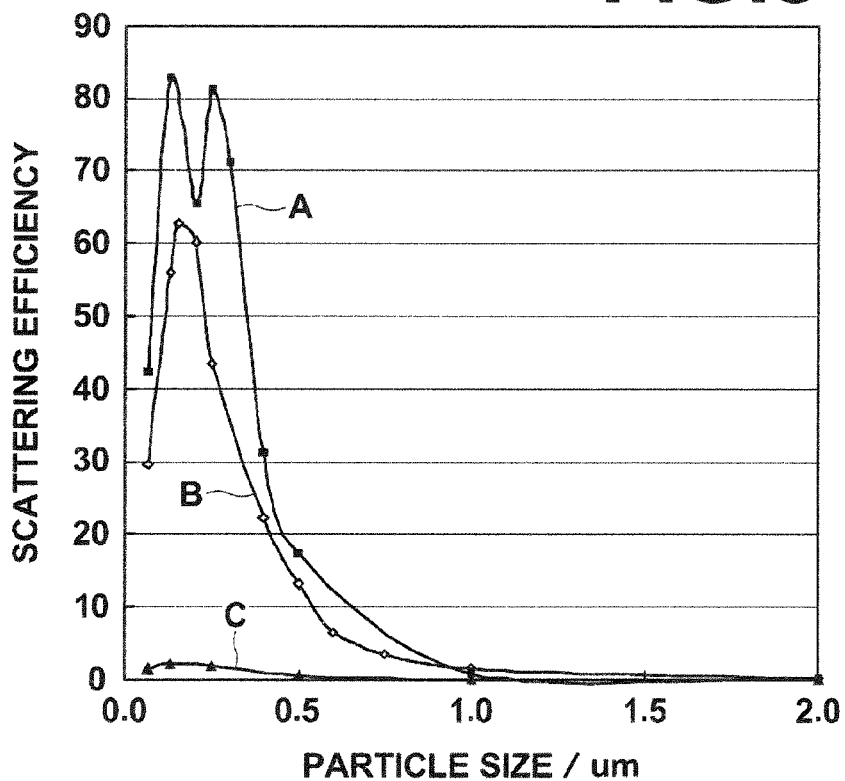
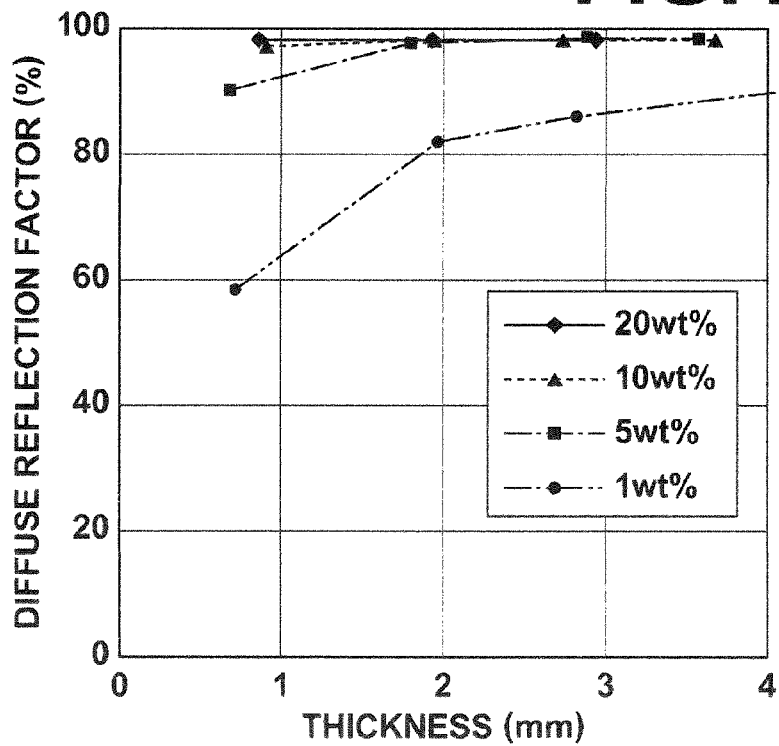

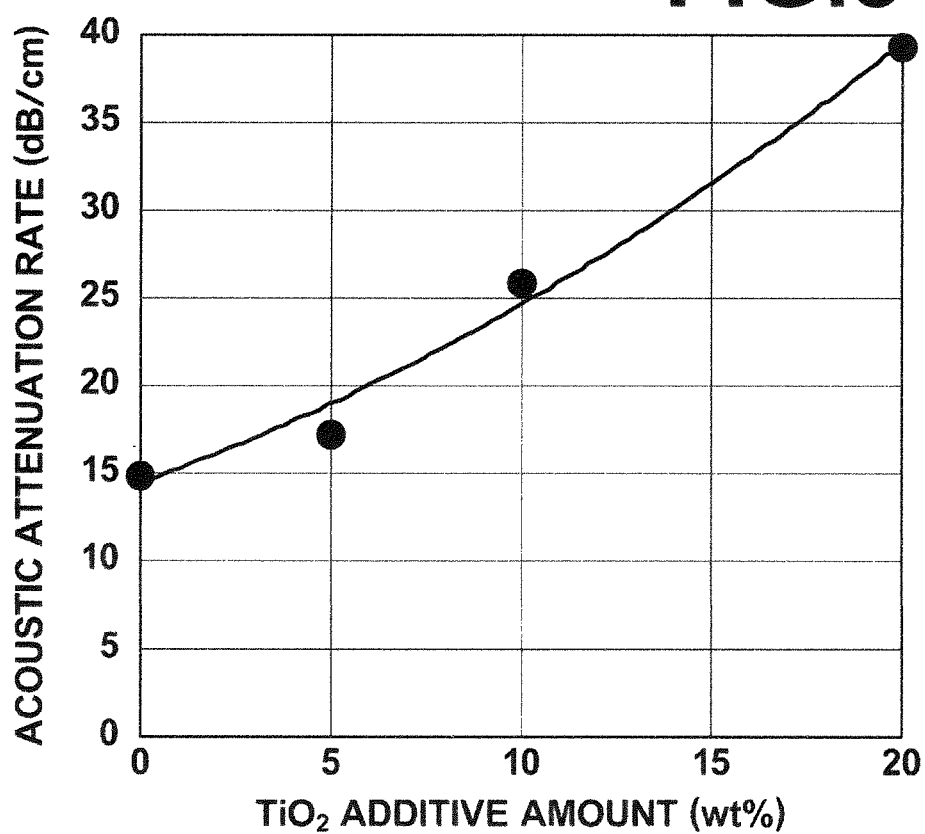

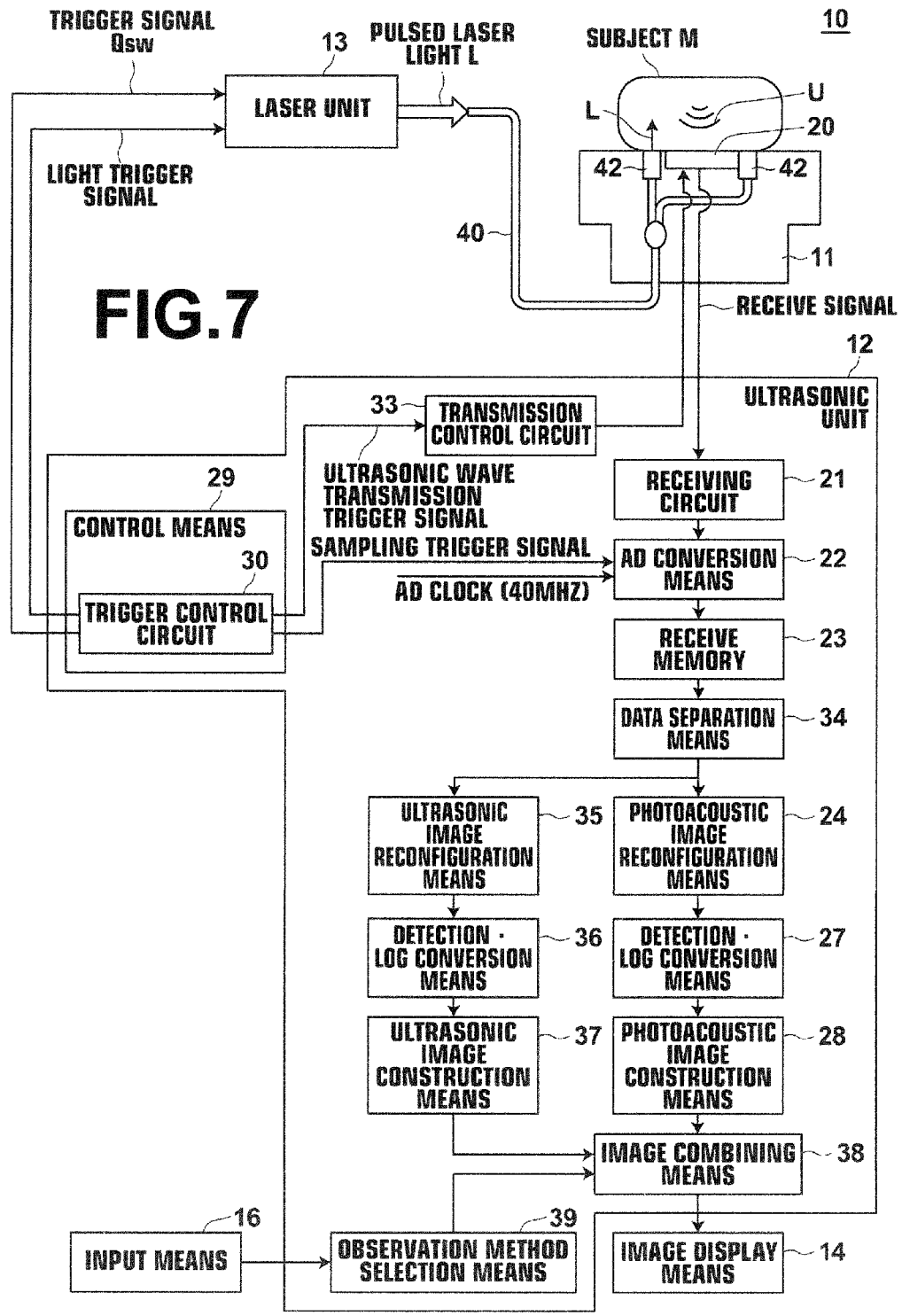

ACOUSTIC WAVE DETECTION PROBE AND PHOTOACOUSTIC MEASUREMENT APPARATUS PROVIDED WITH THE SAME

CROSS-REFERENCE TO RELATED APPLICATIONS

This application is a Continuation of PCT International Application No. PCT/JP2013/000659 filed on Feb. 7, 2013, which claims priority under 35 U.S.C. §119 (a) to Japanese Patent Application No. 2012-028372 filed on Feb. 13, 2012 and Japanese Patent Application No. 2013-019302 filed on Feb. 4, 2013, the contents of which are hereby expressly incorporated herein by reference in their entirety.

TECHNICAL FIELD

The present invention relates to a probe to be applied to a measurement target to detect an acoustic wave, and a photoacoustic measurement apparatus.

BACKGROUND ART

Acoustic wave detection probes have been conventionally used, for example, in ultrasonic imaging devices and photoacoustic imaging devices used for diagnosis, fish finders used in fishery, and the like. Such probes have acoustic lenses incorporated therein for focusing acoustic wave beams to improve resolution.

For example, Japanese Unexamined Patent Publication No. 2005-125071 discloses that the acoustic lens preferably satisfies mainly six characteristics in order to improve contact with a living body. The six specific requirements are: (1) to minimize reflection of ultrasonic waves at a contact portion with a measurement target; (2) to transmit and receive ultrasonic waves with high sensitivity; (3) to be made of a material whose acoustic velocity within the acoustic lens is equal to that within a measurement target (about 1500 m/s) or less so as to have a convex shape; (4) to be made of a material having excellent formability with, in particular, a large tearing strength; (5) constituent material thereof, including an additive, is harmless to living body; and (6) to be made of a material having hardness of a degree that may prevent easy deformation when used.

In order to provide an acoustic lens that satisfy all of the six requirements described above, Japanese Unexamined Patent Publication No. 2005-125071 discloses a composition obtained by mixing a predetermined mass concentration of zinc oxide powder or platinum powder in silicone rubber.

In relation to this, Japanese Unexamined Patent Publication No. 58 (1983)-216294 discloses an acoustic lens obtained by mixing titanium particles with a particle size of 0.08 to 0.20 μm in silicone rubber.

DISCLOSURE OF THE INVENTION

In the meantime, the present inventor has found out a problem in acoustic lenses arising from projection of measuring light in performing photoacoustic measurements. More specifically, if the light reflected from the measurement target passes through the acoustic lens and is absorbed by the acoustic wave transducer, an artifact (virtual image or false image) will appear due to vibration of the acoustic wave transducer, or if the light reflected from a measurement target is absorbed by the acoustic lens, an artifact caused by a photoacoustic wave generated thereat will appear. It is difficult, however, to solve this problem by simply satisfying the six requirements described above.

The present invention has been developed in view of the aforementioned problem and it is an object of the present invention to provide an acoustic wave detection probe capable of reducing the generation of artifacts arising from the projection of measuring light in photoacoustic measurements with a probe, and a photoacoustic measurement apparatus provided with the same.

In order to solve the aforementioned problem, a probe according to the present invention is an acoustic wave detection probe, including:

a light projection section that emits measuring light to be projected onto a subject;

an acoustic wave transducer disposed adjacent to the light projection section and capable of detecting an acoustic wave;

an acoustic lens provided on a detection side of the acoustic wave transducer; and a housing accommodating the light projection section, the acoustic wave transducer, and the acoustic lens, wherein the acoustic lens and a surface portion of the housing adjacent to the acoustic lens have an optical property in which the average diffuse reflection factor is 85% or more and the average absorption factor is 10% or less in a wavelength range of the measuring light.

In the probe according to the present invention, the optical property of the acoustic lens and/or the surface portion of the housing preferably further includes an optical property in which the average diffuse reflection factor in a blue to green wavelength range is 70% or less.

Further, in the probe according to the present invention, the optical property of the surface portion of the housing may be given by a coating material containing a first inorganic pigment. In this case, the first inorganic pigment is preferably at least one type of oxide particles selected from the group consisting of titanium oxide, zirconium oxide, ferric oxide, and cerium oxide. Further, the particle size of the first inorganic pigment is preferably 0.05 to 0.35 μm, and the additive amount of the first inorganic pigment is preferably 2 to 65 wt %.

Still further, in the probe according to the present invention, the optical property of the surface portion of the housing may be given by a diffuse reflection sheet.

Further, in the probe according to the present invention, the optical property of the surface portion of the housing is given by forming the surface portion with a high reflective material. In this case, the high reflective material is preferably a resin which includes an inorganic pigment and at least one type of resin selected from the group consisting of polyester, polyethylene, polycarbonate, polytetrafluoroethylene (PTFE), perfluoroalkoxy fluororesin (PFA), tetrafluoroethylene-hexafluoropropylene copolymer (FEP), ethylene-tetrafluoroethylene copolymer (ETFE), and ethylene-chlorotrifluoroethylene copolymer (ECTFE).

Still further, in the probe according to the present invention, the optical property of the acoustic lens is preferably given by forming the acoustic lens with a material containing a second inorganic pigment. In this case, the second inorganic pigment is preferably at least one type of oxide particles selected from the group consisting of titanium oxide, zirconium oxide, ferric oxide, and cerium oxide. Further, the particle size of the second inorganic pigment is preferably 0.05 to 0.35 μm, and the additive amount of the first inorganic pigment is preferably 2 to 65 wt %. Still further, it is particularly preferable that the material of the acoustic lens is silicone rubber, the second inorganic pigment is titanium oxide particles, and the additive amount of the second inorganic pigment is 5 to 20 wt %.

Further, in the probe according to the present invention, the surface of the housing and/or the acoustic lens is preferably covered with a protective layer.

Still further, in the probe according to the present invention, the wavelength rage of the measuring light is preferably a near infrared wavelength range.

A photoacoustic measurement apparatus according to the present invention includes the probe described above.

The photoacoustic measurement apparatus according to the present invention preferably includes a light source that outputs measuring light in a near infrared wavelength range to be guided to the light projection section of the probe.

Further, the photoacoustic measurement apparatus according to the present invention preferably includes an acoustic image generation means that generates, based on a photoacoustic signal of a photoacoustic wave detected by the probe, a photoacoustic image with respect to the photoacoustic signal.

Still further, in the photoacoustic measurement apparatus according to the present invention, it is preferable that the probe detects a reflected ultrasonic wave of an ultrasonic wave transmitted to the subject and the acoustic image generation means generates an ultrasonic image based on an ultrasonic signal of the reflected ultrasonic wave.

The probe and the photoacoustic measurement apparatus according to the present invention, in particular, the acoustic lens and a surface portion of the housing adjacent to the acoustic lens have an optical property in which the average diffuse reflection factor is 85% or more and the average absorption factor is 10% or less in a wavelength range of the measuring light. This may prevent the light reflected from the measurement target from passing through the acoustic lens and being absorbed by the acoustic wave transducer or being absorbed by the acoustic lens. As a result, the generation of artifacts arising from the projection of measuring light may be reduced in photoacoustic measurements with a probe.

BRIEF DESCRIPTION OF DRAWINGS

FIG. 1A is a schematic front view of a probe of the present embodiment.

FIG. 1B is a schematic side view of the probe of the present embodiment.

FIG. 3 is a schematic view, illustrating the relationship between the particle size of oxide particles and the scattering efficiency.

FIG. 4 is a graph illustrating diffuse reflection factors of silicone rubber containing titanium oxide fine particles with respect to infrared light.

FIG. 5 is a graph illustrating the relationship between the additive amount of titanium oxide fine particles and the acoustic attenuation rate of 7 MHz.

FIG. 7 is a schematic view of a photoacoustic measurement apparatus of a second embodiment, illustrating a configuration thereof.

BEST MODE FOR CARRYING OUT THE INVENTION

Figure 2A:
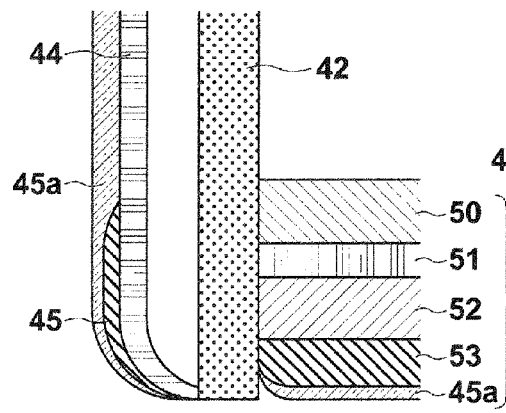
FIG. 2A is a partially enlarged schematic view, illustrating an example configuration of an acoustic lens and a surface portion of the housing adjacent to the acoustic lens.

Hereinafter, embodiments of the present invention will be described with reference to the accompanying drawings, but it should be appreciated that the present invention is not limited to these embodiments. Note that each component in the drawings is not necessarily drawn to scale in order to facilitate visual recognition.

[Embodiment of Acoustic Wave Detection Probe]

An embodiment of acoustic wave detection probe will be described first. FIGS. 1A and 1B are schematic views of the probe of the present embodiment, illustrating a configuration thereof. FIGS. 2A to 2D are partially enlarged schematic views, illustrating example configurations of the acoustic lens and a surface portion of the housing adjacent to the acoustic lens.

As illustrated in FIGS. 1A and 1B, the probe 11 of the present embodiment includes an optical fiber 40, a light guide plate 42, an electroacoustic transducer section 20, and a housing 44 accommodating these. For example, the probe 11 projects laser light L from a light source onto a subject M and detects a photoacoustic wave generated in the subject M by the photoacoustic effect. The wavelength of the laser light is determined appropriately based on the light absorption characteristics of a measurement target substance within the subject M. If the measurement target is a living body, light in a near infrared wavelength range is generally used as the laser light, in view of the absorption characteristics of hemoglobin. The near infrared wavelength range as used herein refers to a wavelength range of about 700 to 850 nm. But it should be appreciated that the wavelength of the laser light is not limited to this.

<Optical Fiber>

The optical fiber 40 is optically connected to a light source that outputs the laser light L and guides the laser light L to the light guide plate 42. There is not any specific restriction on the optical fiber 40 and any known fiber, such as a silica fiber and the like, may be used.

<Light Guide Plate>

The light guide plate 42 is, for example, an acrylic plate or a silica plate with a surface being specially processed to cause light entered from one end to be uniformly surface-emitted from the other end, and corresponds to the light projection section of the present invention. As illustrated in FIG. 1B, in the present embodiment, two light guide plates 42 are disposed so as to face to each other across the electroacoustic transducer section. The optical fiber 40 and the light guide plate 42 are optically coupled. As illustrated in FIG. 1A, a portion of the light guide plate 42 on the side which is coupled to the optical fiber 40 is formed, for example, in a tapered shape. Further, the portion of the light guide plate 42 coupled to the optical fiber 40 is preferably formed of a glass material in order to avoid damage from light energy. The other portion is formed of a resin material, such as acrylic or the like.

The laser light L guided by the optical fiber 40 is incident on the light guide plate 42 and projected onto the subject M from the opposite end. The light guide plate 42 may have, at a tip portion thereof, a mechanism that diffuses light (resin containing scattering particles or the like) or a mechanism that directs the traveling direction of light to the electroacoustic transducer section 20 (notch for refracting light or the like), so that the laser light L can be projected onto a wider range of the subject M.

<Electroacoustic Transducer Section>

The electroacoustic transducer section 20 includes, for example, a backing member 50, an acoustic wave transducer array 51, an acoustic matching layer 52, and an acoustic lens 53.

The backing member 50 serves to absorb acoustic waves transmitted through the acoustic wave transducer array 51 to prevent reflection waves of the acoustic waves from returning to the subject M. For example, the backing member 50 has a composition in which a high density powder material, such as tungsten (W), lead (Pb), zinc oxide (ZnO), or the like is mixed in an epoxy base resin.

The acoustic wave transducer array 51 includes a plurality of acoustic wave transducers disposed one-dimensionally or two-dimensionally and actually convers an acoustic wave signal to an electrical signal. The ultrasonic wave transducer is a piezoelectric element formed, for example, of piezoelectric ceramics or a polymer film, such as a polyvinylidene fluoride (PVDF) film or the like. The term "acoustic wave" as used herein refers to include ultrasonic wave and photoacoustic wave. The term "ultrasonic wave" as used herein refers to an elastic wave generated in the subject by the vibration of the acoustic wave transducer array and a reflection wave thereof, and the term "photoacoustic wave" as used herein refers to an elastic wave generated in the subject by the photoacoustic effect due to the projection of measuring light.

The acoustic matching layer 52 is formed, for example, on a detection plane of the acoustic wave transducer array 51 and serves to match the acoustic impedance. Example materials of the acoustic matching layer include epoxy resin, silica glass, and the like.

The acoustic lens 53 is formed, for example, on the acoustic matching layer 52. The acoustic lens 53 of the present invention has an optical property in which the average disuse reflection factor is 85% or more and the average absorption factor is 10% or less in a wavelength range of the measuring light. The term "wavelength range of the measuring light" as used herein refers to the wavelength range corresponding to the full width at half maximum of the wavelength distribution of the measuring light. For example, the wavelength range of the measuring light in the present embodiment is included in the near infrared wavelength range. The term "average diffuse reflection factor" of the acoustic lens is the diffuse reflection factor at the average thickness of the acoustic lens and refers to the average value of diffuse reflection factors of light belonging to a predetermined wavelength range. The term "average absorption factor" of the acoustic lens is the absorption factor at the average thickness of the acoustic lens and refers to the average value of absorption factors of light belonging to a predetermined wavelength range. The average value of the diffuse reflection factors or absorption factors of light belonging to a predetermined wavelength range may be obtained, for example, by obtaining diffuse reflectance factors or absorption factors of several wavelengths of light belonging to the wavelength range and averaging the respective values. The diffuse reflection factor and absorption factor may be measured by a spectrophotometer or the like. The thickness of the acoustic lens 53 is preferably 0.5 to 2 mm and more preferably 0.7 to 1.5 mm. The reason is that, if it is too thin, it is difficult to obtain a diffuse reflection factor or to form a lens surface with a predetermined density in the wavelength range of the measuring light, while if it is too thick, the absorption by the silicone rubber in the wavelength range of the measuring light is increased.

The aforementioned optical property of the acoustic lens 53 may be given, for example, by forming the acoustic lens 53 with an optically transparent material containing an inorganic pigment. In this case, the inorganic pigment is preferably at least one type of oxide particles selected from the group consisting of titanium oxide, zirconium oxide, ferric oxide, and cerium oxide. In the meantime, as the optically transparent material described above, resin materials such as silicone rubber and the like may be used. As for the silicone rubber, for example, KE-109, KE-106, KE-1031, KE-103, and KE-108 available from Shin-Etsu Chemical Co., Ltd are preferably used. For example, the infrared absorption factor of KE-109 silicone rubber is 1% or less within a preferable thickness range of the acoustic lens 53.

The particle size of the inorganic pigment is controlled appropriately within a range in which generation of artifact, to be described later, is in the electrical noise level and does not cause any problem in image. Further, the particle size of the inorganic pigment is preferably 0.05 to 0.35 μm. This is in consideration of the relationship between the particle size of oxide particles and the scattering efficiency (which is proportional to the reduced scattering constant under the constant particle concentration) shown in FIG. 3. As is known from FIG. 3, high diffuse reflection factors may be obtained in the particle size range of 0.05 to 0.35 μm even the concentration of oxide particles (particle concentration) to the material is low. The graph of FIG. 3 plots calculated values on the assumption of Mie scattering in 756 nm light. Further, the particle size of the inorganic pigment is preferably 0.08 to 0.2 μm if consideration is also given not to reduce the acoustic attenuation rate. The term "particle size" as used herein refers to the average value of diameters of particles of the material type, and may be measured, for example, by the dynamic light scattering method, laser diffraction method, and SEM (Scanning Electron Microscope) imaging method, and the like.

The additive amount of the inorganic pigment is controlled appropriately within a range in which generation of artifact, to be described later, is in the electrical noise level and does not cause any problem in image. The additive amount of the inorganic pigment is preferably 2 to 65 wt %. The reason is that, if the additive amount is lower than the aforementioned range, the average diffuse reflection factor in the wavelength range of the measuring light does not reach 85% within an appropriate thickness range of the acoustic lens 53, while if the additive amount is higher than the aforementioned range, the effect of increasing the average diffuse reflection factor in the wavelength range of the measuring light saturates even the thickness of the acoustic lens 53 is reduced. Further, the additive amount of inorganic pigment is preferably 5 to 20 wt %. The reason why the lower limit is 5 wt % is that the diffuse reflection factor exceeds 85% when the additive amount is 5 wt % within a preferable thickness range of the acoustic lens 53, as shown in FIG. 4. The reason why the upper limit is 20 wt % is that the diffuse reflection factor saturates at about 20 wt %, as shown in FIG. 4, and the acoustic attenuation rate is increased as the additive amount is increased, as shown in FIG. 5, whereby acoustic detection is hindered (i.e., from the viewpoint of acoustic attenuation rate, less additive amount of the inorganic pigment is preferable). FIG. 4 is a graph illustrating diffuse reflection factors of silicone rubber containing particles of a white pigment of titanium oxide (additive amounts in four embodiments are 1 wt %, 5 wt %, 10 wt %, and 20 wt % respectively) with respect to infrared light, in which the horizontal axis represents the thickness (mm) and the vertical axis represents the diffuse reflection factor (%). FIG. 5 is a graph illustrating the relationship between the additive amount of titanium oxide fine particles and the acoustic attenuation rate of 7 MHz, in which the horizontal axis represents the additive amount (wt %) and the vertical axis represents the acoustic attenuation rate (dB/cm).

In designing the acoustic lens 53, it is preferable to give consideration to the acoustic impedance matching between the subject M and the acoustic lens 53. For example, the acoustic impedance of the acoustic lens 53 may be controlled by controlling the additive amount of the inorganic pigment or the other additive agent. For example, if the subject M is a human body, the additive amount of 20 wt %, rather than 5 wt %, for the inorganic pigment may bring the acoustic impedance of each of the subject M and acoustic lens 53 close to each other and acoustic waves may be propagated efficiently.

Generally, if the particle concentration is increased to the extent in which particles come close to a distance of half the particle size or less, the scattering power saturates. For example, if it is assumed that a 0.2 μm particle enters into a cube of 0.3 μm on each side, the scattering power (diffuse reflection factor) saturates, for example, when the volume fraction of inorganic pigment in the mixture of silicone rubber and inorganic pigment is 0.155. Consequently, in the present invention, the additive amount of inorganic pigment is set appropriately within a volume fraction range of 0.155 in the materials constituting the acoustic lens 53. The same applies to the ferric oxide, and the cerium oxide not shown in the graph of FIG. 3.

In the present invention, the acoustic lens 53 preferably has an optical property in which the average diffuse reflection factor in the blue to green wavelength range is 70% or less. The term "blue to green wavelength range" as used herein refers to the wavelength range of about 450 to 550 nm. Such property may be given, for example, by controlling the particle size and the additive amount of the inorganic pigment described above.

<Housing>

The housing 44 is formed, for example, of a copolymerized resin (ABS) of acrylonitrile, butadiene, and styrene, or the like. Although having a hand-held shape in the present embodiment, the housing 44 of the present invention is not limited to this. In the present embodiment, a surface portion of the housing 44 adjacent to the acoustic lens (abutting portion R in FIGS. 1A and 1B in the case of the present embodiment) has an optical property in which the average disuse reflection factor is 85% or more and the average absorption factor is 10% or less in the wavelength range of the measuring light. The term "surface portion adjacent to the acoustic lens" as used herein refers to an area influenced by the light reflected from the target subject and is set, for example, within 1 cm from the acoustic lens, more preferably within 3 cm, and particularly within 5 cm. That is, more advantageous effects of the present invention may be obtained as the area having the optical property of the present invention described above is increased. At least the abutting portion R may have the aforementioned optical property, otherwise the entire housing 44 may have the aforementioned optical property. The term "average diffuse reflection factor" of the abutting portion R is the diffuse reflection factor at the average thickness of the entire members in the abutting portion R and refers to the average value of diffuse reflection factors of light belonging to a predetermined wavelength range. The term "average absorption factor" of the abutting portion R is the absorption factor at the average thickness of the entire members in the abutting portion and refers to the average value of absorption factors of light belonging to a predetermined wavelength range.

The aforementioned optical property in the abutting portion R may be given by applying a coating material containing an inorganic pigment on the abutting portion R, as shown in FIG. 2A. The reference numeral 45 represents a coated film of the coating material formed in the manner described above. In a case where the aforementioned optical property is to be given to the portion of the housing 44 other than the abutting portion R or to the entire portion, the coating material may be applied on the portion where the aforementioned optical property is desired to be given or on the entire portion. In this case, the inorganic pigment is preferably at least one type oxide particles selected from the group consisting of titanium oxide, zirconium oxide, ferric oxide, and cerium oxide. There is not any restriction on the major component of the coating material and a material used commonly as a coating material may be used. The thickness of the coated film is, for example, 0.03 mm or more. The particle size and additive amount of the inorganic pigment are controlled appropriately within ranges in which generation of artifact, to be described later, is in the electrical noise level and does not cause any problem in image. Further, the particle size of the inorganic pigment is preferably 0.05 to 0.35 μm, and the additive amount of the inorganic pigment is preferably 2 to 65 wt %. The reason is the same as in the acoustic lens 53. Further, the housing and/or the acoustic lens may be covered with a protective layer 45a for providing mechanical strength. In this case, the material of the protective layer 45a is preferably a low absorption transparent resin (parylene, silicone resin, polyimide resin, or the like). It is particularly preferable that the coating material described above is, for example, silicone rubber containing titanium oxide particles in the amount of 5 to 20 wt %. The reason is that the use of the silicone rubber as the matrix of the coating material allows the layer assuming the optical property to function also as the protective layer described above.

Figure 2B:
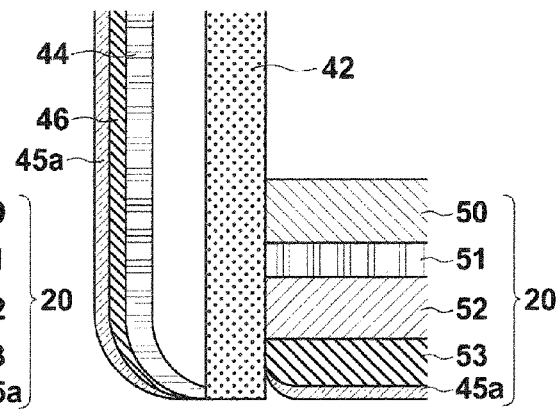
FIG. 2B is a partially enlarged schematic view, illustrating an example configuration of an acoustic lens and a surface portion of the housing adjacent to the acoustic lens.

The aforementioned optical property in the abutting portion R may also be given by applying a diffuse reflection sheet having the aforementioned optical property, as shown in FIG. 2B. The reference numeral 46 in FIG. 2B represents a diffuse reflection sheet applied in the manner described above.

Figure 2C:
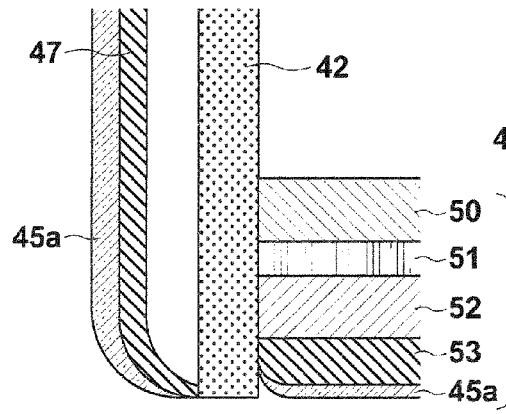
FIG. 2C is a partially enlarged schematic view, illustrating an example configuration of an acoustic lens and a surface portion of the housing adjacent to the acoustic lens.

The aforementioned optical property in the abutting portion R may be given by forming the abutting portion R or the entire housing 44 with a high reflective material, as shown in FIG. 2C. The reference numeral 47 in FIG. 2C represents a housing formed in the manner described above. In this case, the high reflective material is preferably a resin material which includes the aforementioned inorganic pigment. Preferably, the resin material is, for example, polyester, polyethylene, polycarbonate, fluororesins, such as polytetrafluoroethylene (PTFE), perfluoroalkoxy fluororesin (PFA), tetrafluoroethylene-hexafluoropropylene copolymer (FEP), ethylene-tetrafluoroethylene copolymer (ETFE), ethylene-chlorotrifluoroethylene copolymer (ECTFE), and the like, or a combination of two or more of these.

Figure 2D:
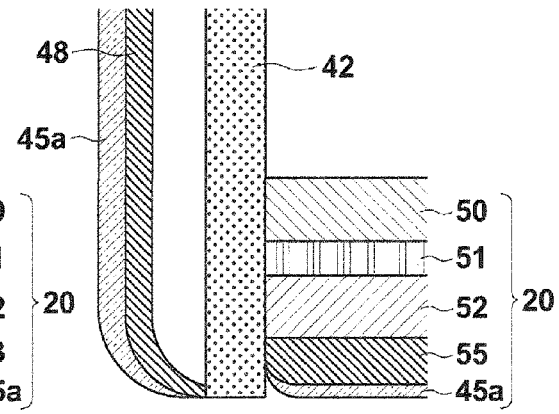
FIG. 2D is a partially enlarged schematic view, illustrating an example configuration of an acoustic lens and a surface portion of the housing adjacent to the acoustic lens.

In the present invention, the optical property of the abutting portion of the housing 44 and/or the acoustic lens 53 preferably includes an optical property in which the average diffuse reflection factor in the blue to green wavelength range is 70% or less. This property may be given by controlling the particle size or the additive amount of the inorganic pigment, or selecting a diffuse reflection sheet having a desired property. For example, FIG. 2D illustrates a housing 48 and an acoustic lens 55 which are controlled in inorganic pigment so as to have an optical property in which the average disuse reflection factor is 85% or more and the average absorption factor is 10% or less in the near infrared wavelength range, and further the average diffuse reflection factor in the blue to green wavelength range is 70% or less. The aforementioned optical property in the blue to green wavelength range is preferably given to the entire housing 44.

<Effects of the Present Invention>

Hereinafter, the effects of the present invention will be described. The probe 11 of the present invention has an optical property, in particular, the acoustic lens 53 and the abutting portion of the housing 44, in which the average diffuse reflection factor is 85% of more and the average absorption factor is 10% or less in the wavelength range of the measuring light.

For example, if the average diffuse reflection factor in the wavelength range of the measuring light is less than 85%, the light reflected from the measurement target passes through the acoustic lens 53 and is absorbed by the acoustic wave transducer array 51, and an artifact (virtual image or false image) caused by vibration of the acoustic wave transducer array 51 will appear. If the average absorption factor in the wavelength range of the measuring light exceeds 10%, the light reflected from the measurement target is absorbed by the acoustic lens 53 and an artifact caused by a photoacoustic wave generated thereat will appear. Therefore, if the acoustic lens 53 has the aforementioned optical property, as in the present invention, the generation of artifact may be inhibited. Further, as the similar problem may occur in the abutting portion of the housing 44 which is likely to be influenced by the reflected measuring light, identical optical property is given also to the abutting portion in the present invention Further, if the average diffuse reflection factor of the abutting portion of the housing 44 and/or the acoustic lens 53 in the blue to green wavelength range exceeds 70%, stains become highly visible when deteriorated in harsh medical environments. It is better, therefore, that the probe 11 is subtly colored (yellow, brown, cream, or the like) rather than pure white in order to make the stains less noticeable. Further, the range of colors that can be used is limited in the medical field. As such, if the housing 44 and the acoustic lens 53 have the aforementioned optical property in the blue to green wavelength range, stains on the probe 11 are less noticeable, so that the probe 11 can be used for an extended period of time in the medical field.

[First Embodiment of Photoacoustic Measurement Apparatus]

Figure 6:
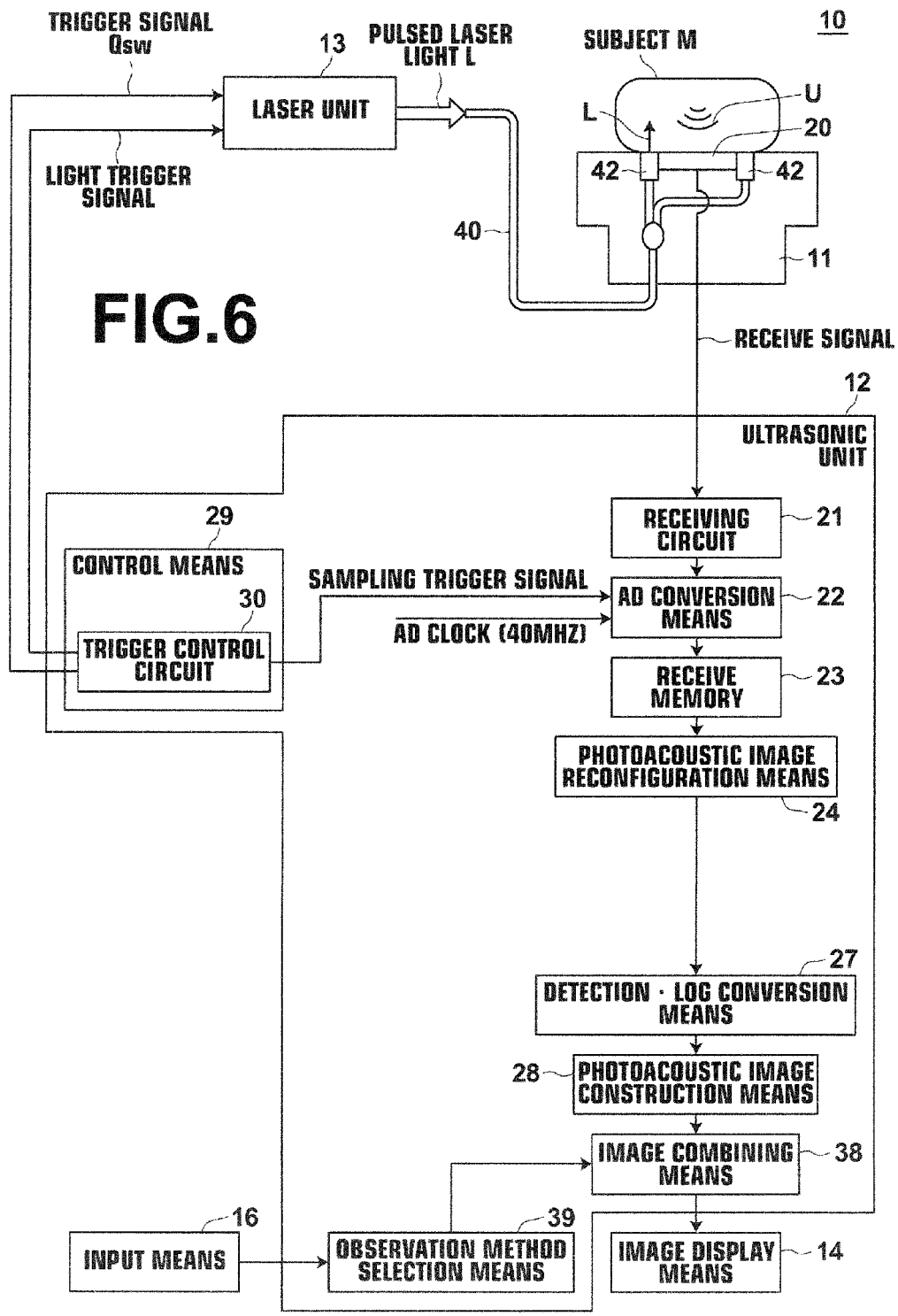
FIG. 6 is a schematic view of a photoacoustic measurement apparatus of a first embodiment, illustrating a configuration thereof.

Next, a first embodiment of photoacoustic measurement apparatus will be described. In the present embodiment, a detailed description will be made of a case in which the photoacoustic measurement apparatus is a photoacoustic image generation apparatus that generates a photoacoustic image based on photoacoustic signals. FIG. 6 is a block diagram of the photoacoustic image generation apparatus 10 of the present embodiment, illustrating the configuration thereof.

The photoacoustic image generation apparatus 10 of the present embodiment includes a probe 11 according to the present invention, an ultrasonic unit 12, a laser unit 13, an image display means 14, and an input means 16.

<Laser Unit>

The laser unit 13 outputs, for example, laser light L as measuring light to be projected onto a subject M. The laser unit 13 is configured to output the laser light L, for example, by receiving a trigger signal from a control means 29. The laser light L outputted from the laser unit 13 is guided to the probe 11 using a light guide means, such as optical fiber, and projected onto the subject M from the probe 11. Preferably, the laser unit 13 outputs pulsed light with a pulse width of 1 to 100 nsec as the laser light.

For example, the laser unit 13 is a Q-switch (Qsw) alexandrite laser in the present embodiment. In this case, the pulse width of the laser light L is controlled, for example, by the Qsw. The wavelength of the laser light is determined appropriately based on the light absorption characteristics of the measurement target substance within the subject. If the measurement target is hemoglobin in a living body (i.e., if blood vessel is imaged) the wavelength, in general, is preferably belongs to near infrared wavelength range. The laser light L may have a single wavelength or a plurality of wavelengths (e.g., 750 nm and 800 nm). If the laser light has a plurality of wavelengths, these wavelengths of light may be projected onto the subject M simultaneously or alternately by switching.

<Probe>

The probe 11 is a probe of the present invention that detects photoacoustic wave U generated in the subject M and, for example, one of the probes shown in FIGS. 1A, 1B and FIGS. 2A to 2D is used.

<Ultrasonic Unit>

The ultrasonic unit 12 includes a receiving circuit 21, an AD conversion means 22, a receive memory 23, a photoacoustic image reconfiguration means 24, a detection. log conversion means 27, a photoacoustic image construction means 28, the control means 29, an image combining means 38, and an observation method selection means 39. The receiving circuit 21, AD conversion means 22, receive memory 23, photoacoustic image reconfiguration means 24, detection•log conversion means 27, and photoacoustic image construction means 28 correspond, as a unit, to the acoustic image generation means of the present invention.

The control means 29 controls each section of the photoacoustic image generation apparatus 10 and includes a trigger control circuit 30 in the present embodiment. The trigger control circuit 30 sends a light trigger signal to the laser unit 13 when, for example, activating the photoacoustic image generation apparatus. This causes a flash lamp in the laser unit 13 to be turned on and excitation of the laser rod is started. The excitation state of the laser rod is maintained and the laser unit 13 becomes ready to output pulsed laser light.

Then, the control means 29 subsequently sends a Qsw trigger signal to the laser unit 13 from the trigger control circuit 30. That is, the control means 29 controls the output timing of the pulsed laser light from the laser unit 13 by the Qsw trigger signal. Further, the control means 29 sends a sampling trigger signal to the AD conversion means 22 simultaneously with the transmission of the Qsw trigger signal in the present embodiment. The sampling trigger signal serves as a timing signal to start sampling of the photoacoustic signal in the AD conversion means 22. In this way, the use of the sampling trigger signal allows the photoacoustic signal to be sampled in synchronization with the output of the pulsed laser light.

The receiving circuit 21 receives a photoacoustic signal detected by the probe 11. The photoacoustic signal received by the receiving circuit 21 is sent to the AD conversion means 22.

The AD conversion means 22 is a sampling means, and samples the photoacoustic signal received by the receiving circuit 21 and converts it to a digital signal. For example, the AD conversion means 22 includes a sampling control section and an AD converter. The receive signal received by the receiving circuit 21 is converted to a digitized sampled signal by the AD converter. The AD converter is controlled by the sampling control section and configured to perform sampling when a sampling trigger signal is received by the sampling control section. The AD conversion means 22 samples the receive signal at a predetermined sampling period based on, for example, an AD clock signal of predetermined frequency inputted from outside.

The receive memory 23 stores the photoacoustic signal sampled by the AD conversion means 22 (i.e., the sampled signal described above). Then, the receive memory 23 outputs the photoacoustic signal detected by the probe 11 to the photoacoustic image reconfiguration means 24.

The photoacoustic image reconfiguration means 24 reads the photoacoustic signal from the receive memory 23 and generates data of each line of a photoacoustic image based on the photoacoustic signal detected by the electroacoustic transducer section 20 of the probe 11. The photoacoustic image reconfiguration means 24 generates data of one line by adding up, for example, data from 64 ultrasonic wave transducers of the probe 11 at delay times corresponding to the positions of the ultrasonic wave transducers (delay-and-sum method). The photoacoustic image reconfiguration means 24 may perform the reconfiguration by the CBP (Circular Back Projection) method in place of the delay-and-sum method. Otherwise, the photoacoustic image reconfiguration means 24 may perform the reconfiguration by the Hough transform method or the Fourier transform method.

The detection•log conversion means 27 obtains an envelope of the data of each line and performs log conversion on the obtained envelope.

The photoacoustic image construction means 28 constructs a photoacoustic image of one frame based on the log-converted data of each line. The photoacoustic image construction means 28 constructs a photoacoustic image, for example, by converting the position of the photoacoustic signal (peak portion) in the time axis direction to the position in the depth direction of the photoacoustic image.

The observation method selection means 39 selects a display mode of the photoacoustic image. As for the display mode of the volume data of photoacoustic signal, for example, a three-dimensional image display mode, a tomographic image display mode, and a graphic display mode on a predetermined axis may be cited. Which display mode is to be used for the display is determined by initial setting or selected according to the user input via the input means 16.

The image combining means 38 generates volume data using the sequentially obtained photoacoustic signals. The generation of the volume data is performed by allocating the signal value of each photoacoustic signal in a virtual space according to the coordinates related to each photoacoustic image frame and pixel coordinates in the photoacoustic image. For example, the coordinate when the Qsw trigger signal is sent, the coordinate when the light is actually outputted, the coordinate when the sampling of the photoacoustic signal is started, and the like are related to each photoacoustic image frame. In allocating signal values, if positions where signal values are to be allocated overlap, for example, an average value or a maximum value of the signals is used as the signal value of the overlapped positions. Further, if no signal value to be allocated is present, an interpolation is preferably performed, as required, using signal values of adjacent positions. For example, the interpolation is performed by allocating a weighted average of four proximal points in order from the most proximal point to the interpolating position. This allows more natural form of volume data to be generated. The image combining means 38 further performs necessary processing (e.g., scale correction, coloring according to the voxel value, and the like) on the generated volume data.

Further, the image combining means 38 generates a photoacoustic image according to the observation method selected by the observation method selection means 39. The photoacoustic image generated according to the selected observation method is the final image to be displayed on the image display means 14 (display image). In the photoacoustic image generation method described above, it should be appreciated that, after a photoacoustic image is generated, the user may rotate or move the image, as required. That is, in the case where a three-dimensional image is displayed, if the user sequentially specifies or moves the direction of viewpoint using the input means 16, the photoacoustic image will be recalculated and the three-dimensional image will be rotated. The user may also change the observation method, as appropriate, using the input means 16.

The image display means 14 displays the display image generated by the image combining means 38.

As described above, the photoacoustic measurement apparatus according to the present embodiment uses a probe of the present invention, so that the generation of artifacts arising from the projection of measuring light may be reduced in photoacoustic measurements with a probe.

[Second Embodiment of Photoacoustic Measurement Apparatus]

A second embodiment of photoacoustic measurement apparatus will be described next. Also in the present embodiment, a detailed description will be made of a case in which the photoacoustic measurement apparatus is a photoacoustic image generation apparatus. FIG. 7 is a block diagram of the photoacoustic image generation apparatus 10 of the present embodiment, illustrating the configuration thereof. The present embodiment differs from the first embodiment in that it generates an ultrasonic image in addition to the photoacoustic image. Therefore, the detailed description of the components identical to those of the first embodiment is omitted unless otherwise specifically required.

The photoacoustic image generation apparatus 10 of the present embodiment includes a probe 11 according to the present invention, an ultrasonic unit 12, a laser unit 13, an image display means 14, and an input means 16, as in the first embodiment.

<Ultrasonic Unit>

The ultrasonic unit 12 of the present embodiment further includes a transmission control circuit 33, a data separation means 34, an ultrasonic image reconfiguration means 35, a detection•log conversion means 36, and an ultrasonic image construction means 37 in addition to the configuration of the photoacoustic image generation apparatus shown in FIG. 6. In the present embodiment, the receiving circuit 21, AD conversion means 22, receive memory 23, data separation means 34, ultrasonic image reconfiguration means 24, detection•log conversion means 27, photoacoustic image construction means 28, ultrasonic image reconfiguration means 35, detection•log conversion means 36, and ultrasonic image construction means 37 correspond, as a unit, to the acoustic image generation means of the present invention.

In the present embodiment, the probe 11 outputs (transmits) an ultrasonic wave to a subject and detects (receives) a reflected ultrasonic wave of a transmitted ultrasonic wave from the subject, in addition to the detection of a photoacoustic signal. As for the ultrasonic wave transducer that performs transmission and reception of ultrasonic waves, the acoustic wave transducer array 51 described above may be used or a new acoustic wave transducer array for transmission and reception of ultrasonic waves provided separately in the probe 11 may be used. Further, the transmission and reception of the ultrasonic wave may be separated. For example, an ultrasonic wave may be transmitted from a position different from the probe 11 and a reflected ultrasonic wave of the transmitted ultrasonic wave may be received by the probe 11.

The trigger control circuit 30 sends an ultrasonic wave transmission trigger signal that instructs transmission of an ultrasonic wave to the transmission control circuit 33 when generating an ultrasonic image. In response to the trigger signal, the transmission control circuit 33 causes an ultrasonic wave to be transmitted from the probe 11. After the transmission of the ultrasonic wave, the probe 11 detects a reflected ultrasonic wave from the subject.

The reflected ultrasonic wave detected by the probe 11 is inputted to the AD conversion means 22 via the receiving circuit 21. The trigger control circuit 30 sends a sampling trigger signal to the AD conversion means 22 in conjunction with the transmission timing of the ultrasonic wave to cause the sampling of the reflected ultrasonic wave to be started. Here, whereas the reflected ultrasonic wave reciprocates between the probe 11 and the ultrasonic wave reflection point, the photoacoustic signal travels one way from the point of generation to the probe 11. As the detection of reflected ultrasonic wave takes twice as long as the detection of a photoacoustic signal generated at the same depth, the sampling clock of the AD conversion means 22 may be reduced to half that of the photoacoustic signal sampling, for example, 20 MHz. The AD conversion means 22 stored a sampled signal of reflected ultrasonic wave in the receive memory 23. Either the sampling of photoacoustic signal or the sampling of reflected ultrasonic wave may precede the other.

The data separation means 34 separates the sampled signal of photoacoustic image from the sampled signal of reflected ultrasonic wave stored in the receive memory 23. The data separation means 34 inputs the separated sampled signal of photoacoustic image to the photoacoustic image reconfiguration means 24. The generation of a photoacoustic image is performed in the same manner as in the first embodiment. In the meantime, the data separation means 34 inputs the separated sampled signal of reflected ultrasonic wave to the ultrasonic image reconfiguration means 35.

The ultrasonic image reconfiguration means 35 generates data of each line of an ultrasonic image based on the reflected ultrasonic waves (sampled signals thereof) detected by a plurality of acoustic wave transducers of the probe 11. For the generation of data of each line, the delay-and-sum method and the like may be used as in the generation of data of each line in the photoacoustic image reconfiguration means 24. The detection•log conversion means 36 obtains an envelope of the data of each line outputted from the ultrasonic image reconfiguration means 35 and performs log conversion on the obtained envelope.

The ultrasonic image construction means 37 generates an ultrasonic image based on the log-converted data of each line.

The image combining means 38 combines the photoacoustic image and the ultrasonic image. For example, the image combining means 38 combines the photoacoustic image and the ultrasonic image by superimposition. The combined image is displayed on the image display means 14. It is also possible to display the photoacoustic image and the ultrasonic image on the image display means side-by-side or by switching, without performing the image combining.

As described above, the photoacoustic measurement apparatus according to the present embodiment also uses a probe of the present invention, so that the generation of artifacts arising from the projection of measuring light may be reduced in photoacoustic measurements with a probe.

Further, the photoacoustic measurement apparatus of the present embodiment generates an ultrasonic image, in addition to a photoacoustic image. Therefore, a portion which cannot be imaged by the photoacoustic image may be observed by referring to the ultrasonic image.

In the foregoing, the description has been made of a case in which the photoacoustic measurement apparatus generates a photoacoustic image or an ultrasonic image. But the image generation is not necessarily required. For example, photoacoustic measurement apparatus may also be configured to measure only the presence or absence of a measuring target based on the magnitude of photoacoustic signal.

What is claimed is:

1. An acoustic wave detection probe, comprising:
    a light projection section that emits measuring light to be projected onto a subject, wherein a wavelength range of the measuring light is a near infrared wavelength range;
    an acoustic wave transducer disposed adjacent to the light projection section and capable of detecting an acoustic wave;
    an acoustic lens provided on a detection side of the acoustic wave transducer; and
    a housing accommodating the light projection section, the acoustic wave transducer, and the acoustic lens,
    wherein the acoustic lens and a surface portion of the housing adjacent to the acoustic lens have an optical property in which the average diffuse reflection factor is 85% or more and the average absorption factor is 10% or less in the wavelength range of the measuring light,
    wherein the optical property of the acoustic lens and/or the surface portion of the housing further includes an optical property in which the average diffuse reflection factor in a blue to green wavelength range is 70% or less.

2. The probe as claimed in claim 1, wherein the optical property of the surface portion of the housing is given by a coating material containing a first inorganic pigment.

3. The probe as claimed in claim 2, wherein the first inorganic pigment is at least one type of oxide particles selected from the group consisting of titanium oxide, zirconium oxide, ferric oxide, and cerium oxide.

4. The probe as claimed in claim 2, wherein the particle size of the first inorganic pigment is 0.05 to 0.35 μm.

5. The probe as claimed in claim 2, wherein the additive amount of the first inorganic pigment is 2 to 65 wt %.

6. The probe as claimed in claim 1, wherein the optical property of the surface portion of the housing is given by a diffuse reflection sheet.

7. The probe as claimed in claim 1, wherein the optical property of the surface portion of the housing is given by forming the surface portion with a high reflective material.

8. The probe as claimed in claim 7, wherein the high reflective material is a resin which includes an inorganic pigment and at least one type of resin selected from the group consisting of polyester, polyethylene, polycarbonate, polytetrafluoroethylene (PTFE), perfluoroalkoxy fluororesin (PFA), tetrafluoroethylene-hexafluoropropylene copolymer (FEP), ethylene-tetrafluoroethylene copolymer (ETFE), and ethylene-chlorotrifluoroethylene copolymer (ECTFE).

9. The probe as claimed in claim 1, wherein the optical property of the acoustic lens is given by forming the acoustic lens with a material containing a second inorganic pigment.

10. The probe as claimed in claim 9, wherein the second inorganic pigment is at least one type of oxide particles selected from the group consisting of titanium oxide, zirconium oxide, ferric oxide, and cerium oxide.

11. The probe as claimed in claim 9, wherein the particle size of the second inorganic pigment is 0.05 to 0.35 μm.

12. The probe as claimed in claim 9, wherein the additive amount of the second inorganic pigment is 2 to 65 wt %.

13. The probe as claimed in claim 12, wherein the material of the acoustic lens is silicone rubber, the second inorganic pigment is titanium oxide particles, and the additive amount of the second inorganic pigment is 5 to 20 wt %.

14. The probe as claimed in claim 1, wherein the surface of the housing and/or the acoustic lens is covered with a protective layer.

15. The probe as claimed in claim 1, wherein the wavelength range of the measuring light is a near infrared wavelength range.

16. A photoacoustic measurement apparatus, comprising the probe as claimed in claim 1.

17. The photoacoustic measurement apparatus as claimed in claim 16, wherein the apparatus comprises a light source that outputs measuring light in a near infrared wavelength range to be guided to the light projection section of the probe.

18. The photoacoustic measurement apparatus as claimed in claim 16, wherein the apparatus comprises an acoustic image generation means that generates, based on a photoacoustic signal of a photoacoustic wave detected by the probe, a photoacoustic image with respect to the photoacoustic signal.

19. The photoacoustic measurement apparatus as claimed in claim 18, wherein:
   the probe detects a reflected ultrasonic wave of an ultrasonic wave transmitted to the subject; and
   the acoustic image generation means generates a ultrasonic image based on an ultrasonic signal of the reflected ultrasonic wave.

* * * * *